United States Patent [19]
Bouhour et al.

[11] Patent Number: 5,645,574
[45] Date of Patent: Jul. 8, 1997

[54] APPARATUS AND PROCESS FOR CONTROL OF IMPLANTABLE RATE-ADAPTIVE CARDIAC PACEMAKER

[75] Inventors: Anne Bouhour, Paris; Thierry Legay, Fontenay les Briis, both of France

[73] Assignee: Ela Medical S.A., Montrouge, France

[21] Appl. No.: 346,027

[22] Filed: Nov. 29, 1994

[30] Foreign Application Priority Data

Dec. 6, 1993 [FR] France ................................ 93 14578

[51] Int. Cl.⁶ .................................................. A61N 1/365
[52] U.S. Cl. ........................................................ 607/17
[58] Field of Search ........................... 607/19, 18, 17, 607/21

[56] References Cited

U.S. PATENT DOCUMENTS

| | | | |
|---|---|---|---|
| 4,966,146 | 10/1990 | Webb et al. | 607/19 |
| 5,031,614 | 7/1991 | Alt | 607/21 |
| 5,074,302 | 12/1991 | Poore et al. | 128/419 PG |
| 5,144,949 | 9/1992 | Olson | 607/17 |
| 5,249,572 | 10/1993 | Bonnet | 607/20 |
| 5,303,702 | 4/1994 | Bonnet et al. | 607/20 |
| 5,312,453 | 5/1994 | Shelton et al. | 607/19 |
| 5,330,510 | 7/1994 | Legay et al. | 607/19 |
| 5,470,344 | 11/1995 | Begemann | 607/17 |

FOREIGN PATENT DOCUMENTS

| | | | |
|---|---|---|---|
| 0498533 | 1/1992 | European Pat. Off. | A61N 1/365 |
| 0493222 | 12/1991 | France | A61N 1/365 |
| 0493220 | 12/1991 | France | A61N 1/365 |
| WO92/03183 | 3/1992 | WIPO | A61N 1/365 |

*Primary Examiner*—William E. Kamm
*Assistant Examiner*—Kennedy J. Schaetzle
*Attorney, Agent, or Firm*—Orrick, Herrington & Sutcliffe LLP

[57] ABSTRACT

A rate-adaptive implantable cardiac pacemaker having a control parameter representative of the physical activity of the patient. The change of the stimulation frequency follows, in a manner to reproduce the natural change of the physiological cardiac rhythm, a non-linear mathematical function of time, e.g., of the type:

$$Fc(t)=A*(1-B*e^{-t/Tau})+C,$$

in which t is time, A, B, C and Tau are constants, and Fc(t) is the stimulation frequency as a function of time. Tau may be a different value for increasing and decreasing frequencies.

39 Claims, 2 Drawing Sheets

APPARATUS AND PROCESS FOR CONTROL OF IMPLANTABLE RATE-ADAPTIVE CARDIAC PACEMAKER

FIELD OF THE INVENTION

This invention relates to an implantable cardiac pacemaker, more specifically to an implantable rate-adaptive pacemaker in which the delivered stimulation frequency changes as a function of one or several control parameters linked to the physical activity of the wearer.

BACKGROUND OF THE INVENTION

There exist rate-adaptive cardiac pacemakers that provide a stimulation rhythm (i.e., a pacing rate) delivered as a function of one or more control parameters linked to the physical activity of the wearer. These control parameters can be, for example, minute ventilation, blood temperature, oxygen concentration of the blood, pH of the blood, vibrations sensed at the pacemaker case, e.g., at the trunk of the wearer, low frequency acceleration at the trunk of the wearer, the QT interval, as well as other measurable parameters indicative of the activity level of the wearer.

Among all of the parameters measured by adequate sensors, the so-called parameter or parameters of enslavement (herein referred to as a "control" parameter), some appear to have a delayed reaction, as compared to that of the physiological cardiac rhythm, in response to a change in activity, and some change more rapidly as compared to the physiological cardiac rhythm. For example, in response to a change in activity, the temperature of the blood will change as an indicator of activity, but more slowly than the natural physiological cardiac rhythm will change in response to that activity. Hence, at an increased stable activity level, the physiological (natural) cardiac rhythm will stabilize before the blood temperature stabilizes. In contrast, sensed accelerations of the trunk will change and stabilize faster than the corresponding physiological cardiac rhythm to a change in the activity level. The relationship between these control parameters and the corresponding cardiac stimulation frequency to be reached, and the monitoring of those control parameters in various forms, are described in the art.

The U.S. Pat. No. 5,074,302 refers to the utilization of a control parameter that has a linear or non-linear relationship function. The document WO 92/03183 refers to relationships associated to one or several parameters. In these descriptions the change over time of the stimulation frequency is not specified in the case where the variation of the control parameter is more rapid than that of the physiological cardiac rhythm. As the inventors have realized, it is necessary to define how the cardiac stimulation frequency is going to change over time from its current value (i.e., a start frequency) to the value calculated based on the measured control parameter(s) (i.e., a calculated target frequency) and a given relationship.

SUMMARY OF THE INVENTION

It is, therefore, an object of the present invention to propose a relationship to determine the evolution or change over time of the stimulation frequency, in a rate-adaptive pacemaker, as a function of a sensed control parameter whose sensed variation is more rapid than the normal physiological response of the cardiac rhythm.

Another object of the invention is to control the profile of evolution of the stimulation frequency of an implanted rate-adaptive pacemaker that is responsive to a control parameter whose variation is more rapid than the physiological cardiac rhythm.

Broadly, the invention concerns a control process and apparatus for a rate-adaptive, implantable cardiac pacemaker which monitors at least one control parameter corresponding to or indicative of the physical activity of the wearer, in which the stimulation frequency follows a non-linear mathematical function dependent on time, which function is an approximation of the evolution of the physiological cardiac rhythm. Stated otherwise, the invention concerns controlling the stimulation frequency evolution between the existing or start frequency and a calculated target frequency that is based on an activity related control parameter, wherein the evolution is a non-linear temporal relationship between the start and target frequency.

In a preferred embodiment the non-linear relationship is a mathematical function of the type:

$$Fc(t)=A*(1-B*e^{-t/Tau})+C,$$

where Fc(t) is the stimulation frequency delivered by the pacemaker as a function of time, t is the parameter of time, and A, B, C, and Tau are predetermined constants.

In another embodiment, the mathematical function is a hyperbolic function of the type:

$$Fc(t)=K-(Tau/t).$$

where K and Tau are predetermined constants and t is the parameter of time.

The non-linear mathematical function may be separately considered for increasing and decreasing stimulation frequencies, for example, as the following set of homogeneous equations:

$$Fc(t)=(Fstart-Ftarget)e^{-t/Tau\_inc}+Ftarget, \qquad (1)$$

to control the increase (acceleration) of the stimulation frequency, and $$Fc(t)=(Fstart-Ftarget)e^{-t/Tau\_dec}+Ftarget, \qquad (2)$$

to control the decrease (deceleration) of the stimulation frequency, wherein:

Fstart is the existing stimulation frequency from which the calculated increase or decrease of the stimulation frequency changes, Ftarget is the stimulation frequency that has to be reached, as calculated based on the value of the one or more control parameters representative of activity, Tau_inc is a control parameter for an increase of the stimulation frequency from Fstart to Ftarget;

Tau_dec is a control parameter for a decrease of the stimulation frequency from Fstart to Ftarget.

Tau_inc may be different from Tau_dec so that an increase in stimulation frequency over time will have a different change profile than a decrease in frequency, even as between the same two frequency bounds. This advantageously permits a more accurate approximation of the natural physiological cardiac rhythm under the same circumstances of activity change.

The above mathematical functions are preferably implemented in pacemakers which control pacing by use of escape intervals by transforming the frequency-based equations to apply to calculating cardiac escape intervals. This permits the calculation of the escape interval for the following cardiac cycle by adding to the current escape interval a variation:

$$dTc(t)=Tc^3(t)*[Fc(t)-Ftarget]/Tau,$$

where Tc(t)=1/Fc(t); Tau=Tau_inc, for a frequency increase; Tau=Tau_dec, for a frequency decrease.

Preferably, the variation dTc(t) is not systematically added to each escape interval. Rather, it is added to an existing escape interval only after passage of a selected number of escape intervals, where the selected number is a variable "MULT". Hence, to apply the variation dTc(t) to a variable number of escape intervals, the variation is calculated in the following manner:

$$dTc(t)=Round(MULT*Tc^3(t)*[Fc(t)-Ftarget]/Tau),$$

where the factor MULT is obtained by an algorithm. The term Round refers the mathematical function of rounding to an integer value. In one such algorithm, the factor MULT:

is incremented when the variation applied on the preceding escape interval is null (zero), is reset to 1 as soon as the variation is non null (non zero), and is reset to 1 if Fc=Ftarget.

The allowed variation of the stimulation frequency for a given cardiac cycle to the following cardiac cycle is limited to a maximal value, equal preferably to 6 mn$^{-1}$. The term mn$^{-1}$ means beats per minutes in accordance with ISO standards. This minimizes the likelihood of stimulating the heart with an acceleration or deceleration that is unhealthy.

The invention also is directed to an implantable rate-adaptive implantable cardiac pacemaker having a sensor for monitoring a control parameter representative of the physical activity of the wearer, and a processor to calculate a stimulation frequency corresponding to the sensed control parameter value, characterized in that, the evolution of the stimulation frequency follows in a manner to reproduce the evolution of the physiological cardiac rhythm, as a non-linear mathematical function of time. One such mathematical function is preferably of the type:

$$Fc(t)=A*(1-B*e^{-t/Tau})+C,$$

where Fc(t) is the cardiac frequency delivered by the pacemaker as a function of time, t is the parameter of time, and A, B, C, and Tau are constants. Such a pacemaker may be a single or dual chamber pacemaker, and implement the function by calculating escape intervals using timers/counters, a microprocessor executing software instructions, solid state circuits or some combination thereof, to perform the data acquisition and processing functions described herein.

BRIEF DESCRIPTION OF THE DRAWINGS

Further features of the invention, its nature and various advantages will be more apparent from the accompanying drawings and the following detailed description of the invention, in which like reference numerals and characters refer to like elements and parameters, and in which.

DETAILED DESCRIPTION OF THE INVENTION

The invention applies to a rate-adaptive cardiac pacemaker which senses and is thus controlled by one or several sensed parameters that are representative of the physical activity of the wearer of the pacemaker. The pacemaker may be a single or double chamber pacemaker and possesses all current functionalities of such a rate-adaptive cardiac pacemaker.

A clinical study concerning conduct of the present invention has shown that during the efforts of daily life (rest, walking, rapid walking, climbing steps, running, etc.), subjects have to provide a constant power level during the effort, whose amplitude corresponds to the type of effort undertaken. On the other hand, for each of these efforts, the physiological cardiac rhythm accelerates or decelerates following a well-defined profile until it reaches a representative level of the power of the effort.

Figure 1A:
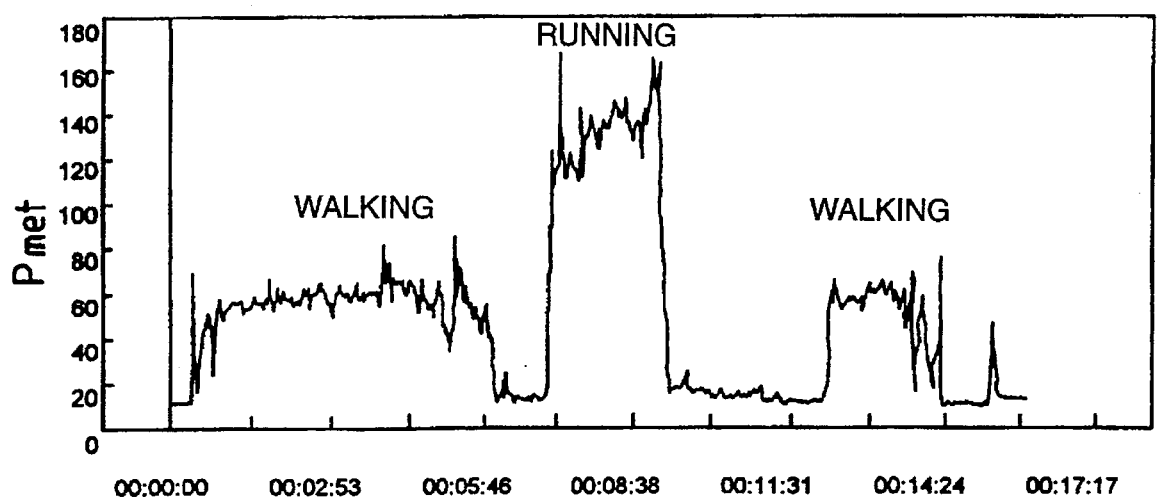
FIG. 1A represents the sensed magnitude versus time of a representative parameter of the activity of a person in the course of various phases of rest, medium activity (walking), and intense activity (race)
Figure 1B:
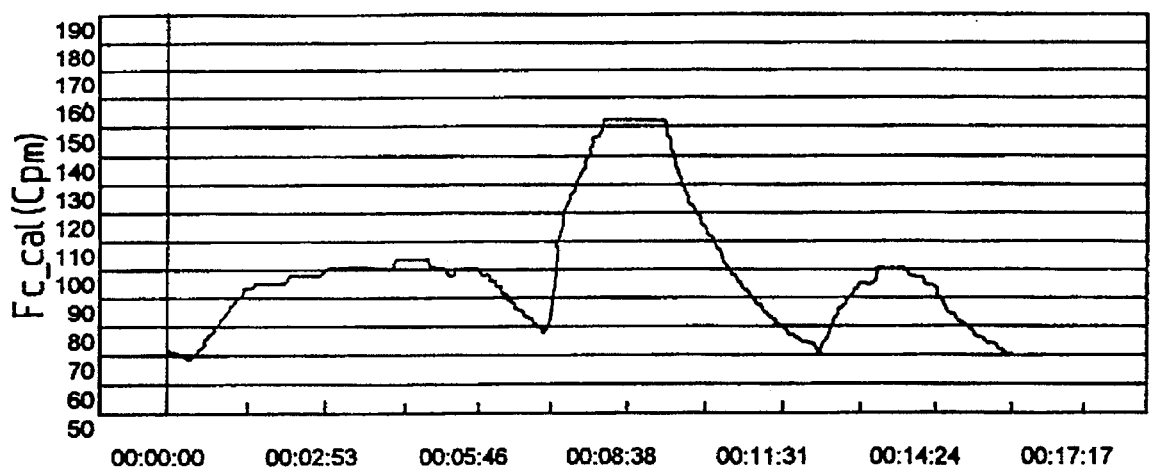
FIG. 1B represents a calculated cardiac stimulation frequency versus time determined in accordance with an embodiment of the present invention, corresponding to the same periods of rest, medium activity, and intense activity shown in FIG. 1A.
Figure 1C:
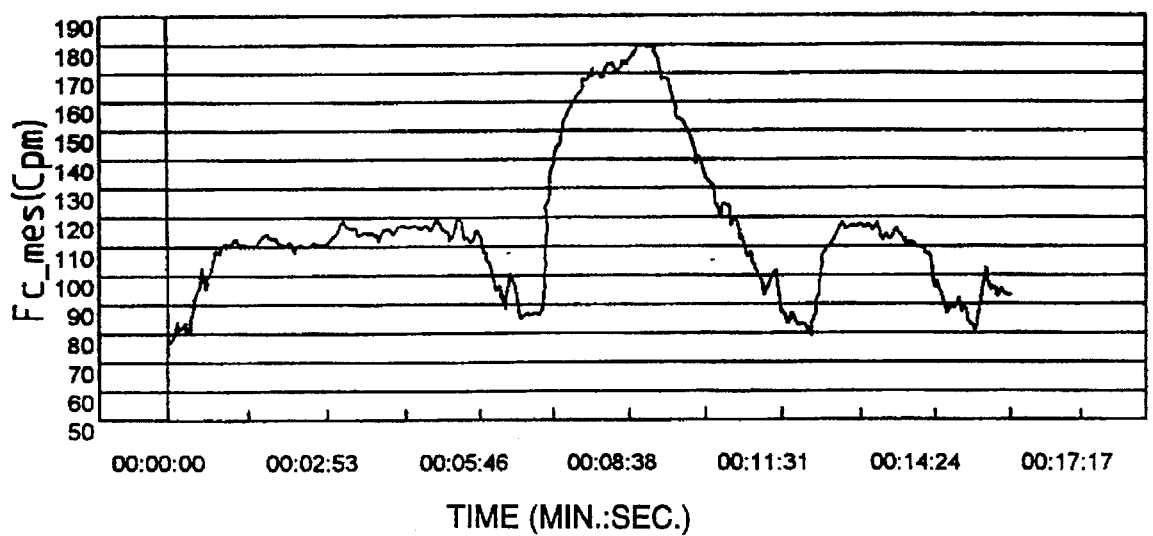
FIG. 1C represents a measured physiological (natural) cardiac rhythm versus time of a subject without cardiac pathology, measured by an external electrocardiogram, corresponding to the same periods of rest, physical activity and intense activity shown in FIG. 1A.

The present invention is particularly efficient to control the profile of change of the stimulation frequency of a rate-adaptive pacemaker having a control parameter whose reaction is more rapid than the corresponding physiological change of the cardiac rhythm. FIGS. 1A and 1C show an example of the comparative change of the physical activity control parameter and the corresponding physiological cardiac rhythm. In accordance with the invention, a cardiac stimulation frequency is provided whose profile of change over time, for the acceleration and the deceleration (FIG. 1b) is similar to the physiological cardiac rhythm profile of change over time (FIG. 1c). The crude signal delivered by the one or more sensors monitoring one or more activity control parameters, is or are processed by an electronic circuit (hardware) and/or software to provide the control parameters for determining the stimulation frequency. The value of the one or more control parameters permits calculating the value of the frequency (Fcapt) that is the cardiac stimulation frequency that has to be reached after the transitory regime.

The transfer function, used in the described application, between the value of the control parameter and that of the corresponding cardiac stimulation frequency, is a linear relationship of the type: Fcapt=A*parameter+b, where a and b are constants programmed by the physician and/or determined in an automatic manner according to the daily activity of the wearer. The relationship between Fcapt and the parameter can of course be another relation. The parameter used in a preferred embodiment is the integral, calculated over 1.56 seconds, of the absolute value of the signal of acceleration measured in the anterior-posterior axis by an accelerometer as a variation of capacity. This is described more completely in U.S. Pat. Nos. 5,249,572, 5,303,702 and 5,330,510, the disclosures of which are incorporated herein in their entirety. This control parameter provides a representative level of the level of power developed by the subject at the given effort (activity), and has a response that is more rapid than the natural physiological cardiac response. The invention advantageously corrects this problem by determining a variation profile that is or approximates a physiological profile.

The implementation of the invention is preferably made by implementing software instructions, executed by a microprocessor of the known cardiac pacemakers, for processing the digitized sensed and calculated signals. The invention also could be implemented in a solid state circuits adapted for digital processing and manipulations of the signals. The implementation is believed to be within the abilities of a person of ordinary skill in the art.

According to FIG. 1c, as well as the reported medical literature, the change of the cardiac rhythm of a submissive subject to an effort of a constant power level (as in walking) is very well correlated with a mathematical formula of the form:

$$Fc(t)=A\{1-B*e^{-t/Tau}\}+C,$$

in which F(c)t is the frequency of stimulation, t is the parameter time, and A, B, C and Tau are constants, which may be adjustable or programmable.

According to the invention, this formula is chosen such that for an indicated increase in stimulation frequency:

$$Fc(t)=(Fstart-Ftarget)*e^{-t/Tau\_inc}+Ftarget,$$

and for an indicated decrease in stimulation frequency:

$$Fc(t)=(Fstart-Ftarget)*e^{-t/Tau\_dec}+Ftarget,$$

where Ftarget is the stimulation frequency that has to be reached that is given by the control parameter, and Ftarget=Fcapt; Fstart can be the stimulation frequency of rest or the maximal stimulation frequency or the current stimulation frequency; Tau_inc is a parameter for control of the rate of increase (acceleration), and Tau_dec is a parameter for control of the rate of decrease (deceleration). These two Tau parameters are determined as a function of the choice of the physician for the patient. Importantly, these two equations are identical (although the Tau constants may be different), which allows a homogeneous processing of the acceleration and deceleration profiles of the cardiac stimulation frequency.

In practice, most pacemakers control the escape interval rather than the stimulation frequency. Therefore, the foregoing is implemented by calculating escape intervals or periods (Tc=1/Fc). At each time of calculation, one is interested in the variation dTc that is to be applied to the known value of the existing escape interval to calculate the duration of the following escape interval for the next cardiac cycle. One is particularly interested in differentials of these equations (calculated as periods) as follows.

For the increase of cardiac frequency:

$$\frac{dTc(t)}{dt} = \frac{-F'c(t)}{Fc^2(t)} \qquad (1)$$

$$= -Tc^2(t) * [-1/Tau\_inc * (Fstart-Ftarget) * e^{-t/Tau\_inc}]$$

$$= 1/Tau\_inc * Tc^2(t) * [Fc(t)-Ftarget] < 0$$

for the decrease of cardiac frequency:

$$\frac{dTc(t)}{dt} = -Tc^2(t) * [-1/Tau\_dec * (Fstart-Ftarget) * e^{-t/Tau\_dec}]$$

$$= 1/Tau_{dec} * Tc^2(t) * [Fc(t)-Ftarget] > 0$$

The time interval dt, where these calculations are realized represents the minimum cardiac escape interval: dt=Tc(t).

Relationships (1) and (2) become in this case:

$$dTc(t)=1/Tau\_inc*Tc^3(t)*[Fc(t)-Ftarget]<0 \qquad (3)$$

$$dTc(t)=1/Tau\_dec*Tc^3(t)*[Fc(t)-Ftarget]>0 \qquad (4)$$

It is always simpler to have dTc>0, and to subtract it from the current escape interval running for an increasing frequency, and to add it for a decreasing frequency. In this case, relationships (3) and (4) become:

$$dTc(t)=1/Tau\_inc*Tc^3(t)*[Ftarget-Fc(t)]>0 \qquad (5)$$

$$dTc(t)=1/Tau\_dec*Tc^3(t)*[Fc(t)-Ftarget]>0 \qquad (6)$$

with dTc, Tau, Tc expressed in seconds and Ftarget and Fc in Hertz. For the described application, escape intervals are expressed in units of 15.625 ms and frequencies in $mn^{-1}$. Hence, relationships (5) and (6) become:

$$dTc(t)=Round\{1/Tau\_inc*Tc^3(t)*[Ftarget-Fc(t)]/3840\}>0 \qquad (7)$$

$$dTc(t)=Round\{1/Tau\_dec*Tc^3(t)*[Fc(t)-Ftarget]/3840\}>0 \qquad (8)$$

In the application described, the smallest possible value for dTc is 15.625 ms (1 unit). However, between two consecutive cardiac cycles in the description of the profile, in order to approach the limit of Ftarget, values smaller than 15.625 ms may need to be used. This problem is solved by not applying dTc on each cardiac cycle, but rather on a multiple of a cycle, such as on every 3, 4 cycles, etc., according to a multiplication coefficient MULT that increments each time that dTc is equal to 0 (0 unit).

The introduction of this coefficient MULT has to be understood as a multiplication of the calculation interval dt of equations (1) and (2). The transition to equations (3) and (4) is made by taking dt=MULT*Tc(t). When the calculation of dTc(t) gives values non null, MULT=1; and as soon as dTc(t) is zero the value MULT is incremented at each calculation of an escape interval until it obtains a non null value of dTc; from then on the multiplication value MULT is reset to 1 for the following cycles. As soon as the limit Ftarget is reached, the multiplication value MULT is reset to 1. The foregoing algorithm controls the variable MULT to obtain the result of smaller time interval increments than 15.625 ms.

Relationships (7) and (8) thus become:

$$dTc(t)=Round\{MULT/Tau\_inc*Tc^3(t)*[Ftarget-Fc(t)]/3840\}>0 \qquad (9)$$

$$dTc(t)=Round\{MULT/Tau\_dec*Tc^3(t)*[Fc(t)-Ftarget]/3840\}>0 \qquad (10)$$

In order to prevent the occurrence of too large a gap in the cardiac frequency between two consecutive cycles, the permitted variation of the cardiac stimulation frequency from one cycle to the following cycle is limited to a maximal value ($V_{max}$). The multiplication value MULT is reset to 1 if the limit is applied. This value $V_{max}$ is preferably equal to 6 $mn^{-1}$.

Figure 2:
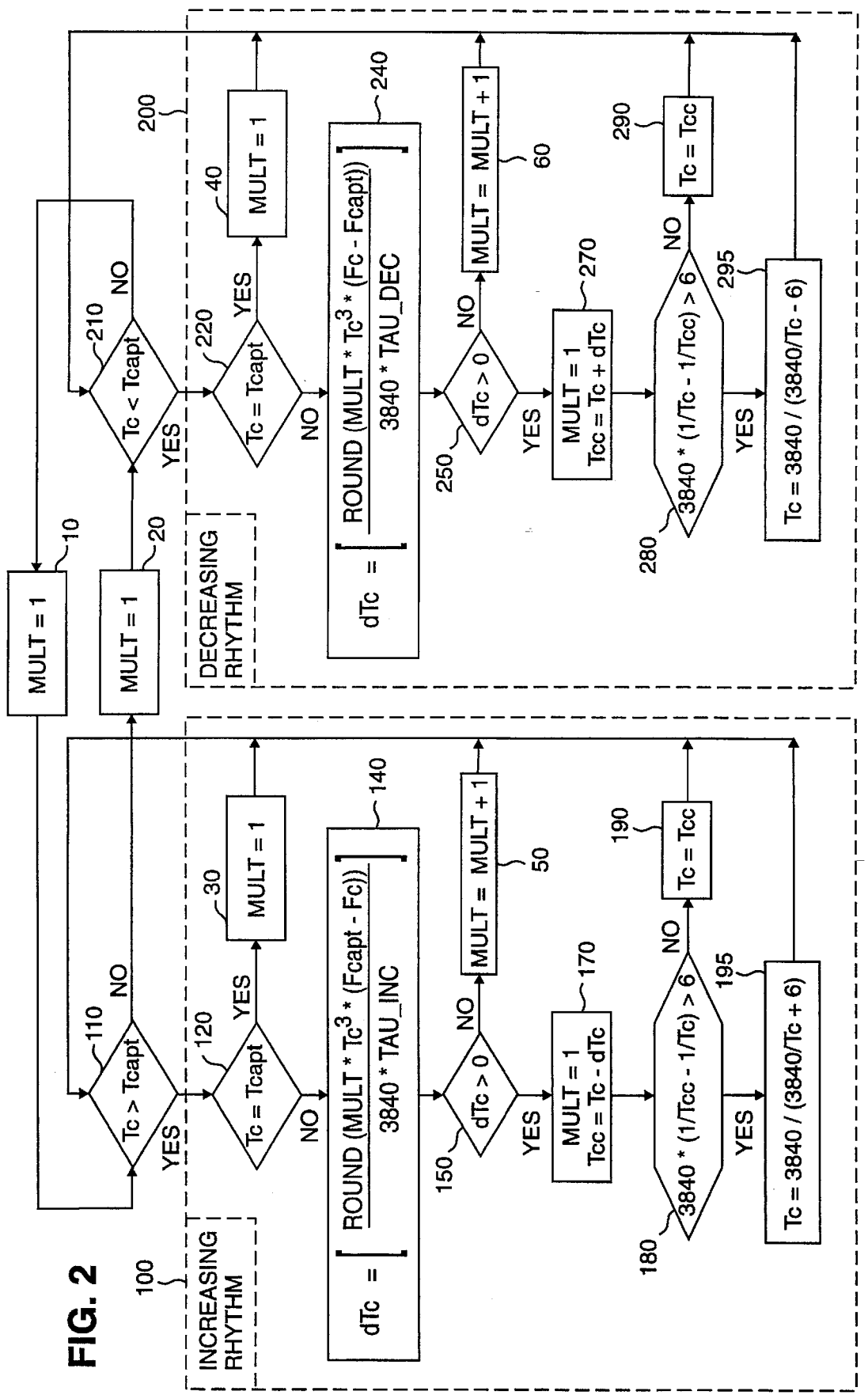
FIG. 2 represents a schematic flow chart for controlling the cardiac stimulation frequency in accordance with an embodiment of the present invention, applicable to the determination of the stimulation frequency of FIG. 1B to approximate the cardiac rhythm of FIG. 1C.

Referring to FIG. 2, a flow chart for the control of the cardiac stimulation frequency profile exploiting equations (9) and (10) is shown. The control process manages the increase (Box 100) and the decrease (Box 200) of the stimulation frequency to approximate the physiological cardiac rhythm. The calculated target frequency interval Tcapt (also referred to as Ftarget) is compared to the current interval Tc in steps 110, 120, 210 and 220 to determine which Box to use, and whether the MULT variable is reset to 1 as indicated in steps 10, 20, 30, and 40. The escape interval of the following cycle is then calculated as a function of existing escape interval Tc by:

(1) in increasing cases: Tc(t+1)=Tc(t)−dTc(t) (step 170), with dTc(t) given by equation (9) (step 140), and (2) in decreasing cases: Tc (t+1)=Tc(t)+dTc(t) (step 270), with dTc(t) given by equation (10) (step 240).

The symbol Tcc used in FIG. 2 steps 170, 180, 190, 270, 280 and 290, designates the next cardiac period (escape interval) calculated. The variation dTc is tested relative to 0 in steps 150 and 250, such that the variable MULT is increased at steps 50 and 60 if appropriate or reset and Tcc calculated at steps 170 and 270. The acceleration/deceleration limits ($V_{max}$) are tested at steps 180 and 280, with the appropriate calculated interval Tcc (steps 190 and 290) or the limited interval (steps 195 and 295) applied, as appropriate.

In the application of the present invention, the limit Fcapt=Ftarget is calculated every 1.56 s, independently of the calculation of escape intervals. It is used during calculation of the following escape interval. This limit can vary from one escape interval to the next without provoking any discontinuity in the calculation of the cardiac stimulation frequency (or the corresponding escape interval) because the two homogeneous equations of the increase and the decrease insure the mathematical continuity.

This principle of control of the cardiac stimulation frequency allows obtaining profiles of a calculated cardiac stimulation frequency (FIG. 1b) similar to a physiological rhythm profile acquired during walking or running efforts for subjects without any cardiac pathology (FIG. 1c).

According to the invention, the mathematical functions advantageously redirect the stimulation frequency to follow the change of a natural physiological cardiac rhythm thereby to provide a more normal heartbeat profile. This is useful to allow for natural cardiac activity to resume, so that paced activity can be suspended whenever possible, and so that the patient feels normal even when paced activity occurs.

In the example described above, the mathematical function is the typical exponential relation of $Fc(t)=A*(1-B*e^{-t/Tau})+C$. This function can be replaced by others functions that represent an approximation of the change of the physiological cardiac rhythm. A number of examples within the framework and scope of the invention, of such mathematical functions, include:

$$Fc(t)=K+K'*t/Tau*[1-t/(2\ Tau)] \text{ and}$$

$$Fc(t)=K-(Tau/t).$$

These functions are non-linear functions that depend on time, and not the control parameter corresponding to patient activity wherein Tau, K and K' are predetermined constants.

One skilled in the art will appreciate that the present invention can be practiced by other than the described embodiments which are presented for purposes of illustration and not of limitation.

We claim:

1. A method of controlling an implantable cardiac pacemaker having a stimulation frequency that is a function of at least a parameter representative of the physical activity of a patient, comprising adjusting the stimulation frequency to follow a time dependent non-linear mathematical function that is an approximation of the change of the physiological cardiac rhythm.

2. The process according to claim 1, characterized in that the mathematical function is of the type:

$$Fc(t)=A*(1-B*e^{-t/Tau})+C,$$

where Fc(t) is the stimulation frequency delivered by the pacemaker as a function of the time, t is the parameter of time, and A, B, C, and Tau are constants.

3. The process according to claim 2, characterized in that said mathematical function is approximated by a boundary limit.

4. The process according to claim 1, characterized in that the mathematical function is of the type:

$$Fc(t)=K-(Tau/t).$$

5. The process according to claim 2, characterized in that the mathematical function is the type:

$Fc(t)=(Fstart-Ftarget)*e^{-t/Tau\_inc}+Ftarget$, to control an increase of the stimulation frequency, and $Fc(t)=(Fstart-Ftarget)*e^{-t/Tau\_dec}+Ftarget$, to control a decrease of the stimulation frequency, where Fstart is the cardiac stimulation frequency from which the increase or decrease of the stimulation frequency is measured, Ftarget is the calculated, cardiac stimulation frequency that has to be reached based on the sensed value of one or more control parameters of the pacemaker, Tau_inc is a control parameter of the increase of the stimulation frequency from Fstart to Ftarget; and Tau_dec is a control parameter of the decrease of the stimulation frequency from Fstart to Ftarget.

6. The process according to claim 5, characterized in that said mathematical function is transformed to calculate cardiac escape intervals and to permit the calculation of the following escape interval by applying to the prior escape interval a variation:

$$dTc(t)=Tc^3(t)*[Fc(t)-Ftarget]/Tau,$$

where Tc(t)=1/Fc(t); Tau=Tau_inc, for an increase of the stimulation frequency, and Tau=Tau_dec, for a decrease of the stimulation frequency.

7. The process according to claim 6, characterized in that the variation dTc(t) is not systematically applied to each escape interval but is applied to an escape interval every variable number (MULT) of escape intervals.

8. The process according to claim 7, characterized in that said variation dTc(t) applied on a variable number of escape intervals, is calculated as:

$$dTc(t)=Round(MULT*Tc^3(t)*[Fc(t)-Ftarget]/Tau),$$

where the factor MULT is obtained by an algorithm.

9. The process according to claim 8, characterized in that the factor MULT:

is incremented when variation applied to the preceding escape interval is null, is reset to 1 as soon as the said variation is non null, and is reset to 1 if Fc=Ftarget.

10. The process according to claim 9, characterized in that the permitted variation of the cardiac stimulation frequency from one cycle to the following cycle is limited to a maximal value, preferably equal to 6 $mn^{-1}$.

11. An implantable rate-adaptive cardiac pacemaker having a sensor detecting at least a parameter representative of the physical activity of a patient and a processor for determining, as a function of the detected parameter, a cardiac stimulation frequency which follows, in a manner to reproduce a change of a physiological cardiac rhythm, a mathematical function of the type:

$$Fc(t)=A*(1-B*e^{-t/Tau})+C,$$

where Fc(t) is the stimulation frequency output by the pacemaker as a function of time, t is the parameter of time, and A, B, C, and Tau are constants.

12. The apparatus according to claim 11, characterized in that the mathematical function is of the type:

$$Fc(t)=(Fstart-Ftarget)*e^{-t/Tau\_inc}+Ftarget,$$

to control an increase of the stimulation frequency output, and $$Fc(t)=(Fstart-Ftarget)*e^{-t/Tau\_dec}+Ftarget,$$

to control a decrease of the stimulation frequency output, where:

Fstart is the cardiac stimulation frequency from which the increase or the decrease of the stimulation frequency output begins, Ftarget is the calculated cardiac stimulation frequency that has to be reached based on the sensed value of one or more control parameters of the pacemaker, Tau_inc is a control parameter of the increase of the stimulation frequency output from Fstart to Ftarget, Tau_dec is a control parameter of the decrease of the stimulation frequency output from Fstart to Ftarget.

13. The apparatus according to claim 12, characterized in that the mathematical function is transformed to calculate a cardiac escape interval and to permit the calculation of the following escape interval wherein the processor further comprises means for applying to the prior escape interval a variation:

$$dTc(t)=Tc^3(t)*[Fc(t)-Ftarget]/Tau,$$

where Tc(t)=1/Fc(t), Tau=Tau_inc, for the increase of the stimulation frequency output, and Tau=Tau_dec, for the decrease of the stimulation frequency output.

14. The apparatus according to claim 13, characterized in that the variation dTc(t) is not systematically applied to each escape interval but is applied to an escape interval every variable number (MULT) of escape intervals.

15. The apparatus according to claim 14, characterized in that variation dTc(t) applied every variable number of escape intervals is calculated as $$dTc(t)=Round(MULT*Tc^3(t)*[Fc(t)-Ftarget]/Tau),$$

where the factor MULT is obtained by an algorithm.

16. The apparatus according to claim 15, characterized in that the factor MULT:

is incremented when the variation applied on the preceding escape interval is null, is reset to 1 as soon as the variation is non null, and is reset to 1 if Fc=Ftarget.

17. The apparatus according to claim 16, characterized in that the variation of the cardiac stimulation frequency from one cycle to the following cycle is limited to a maximal value, preferably equal to 6 mn$^{-1}$.

18. A method of controlling an implantable rate-adaptive cardiac pacemaker having a delivered stimulation frequency and a calculated stimulation frequency that is periodically calculated as a function of a sensed control parameter representative of the physical activity of a patient, comprising:

comparing an existing delivered stimulation frequency and a calculated stimulation frequency (Ftarget); and controlling the delivered stimulation frequency to change between Fstart and Ftarget as a dependent non-linear mathematical function of time, wherein said function approximates a physiological cardiac rhythm change over time.

19. The method of claim 18 wherein the controlling step further comprises calculating the delivered stimulation frequency according to a mathematical function of the type:

$$Fc(t)=A*(1-B*e^{-t/Tau})+C,$$

where Fc(t) is the delivered stimulation frequency to be delivered by the pacemaker as a function of the time, t is the parameter of time, and A, B, C, and Tau are predetermined constants.

20. The method of claim 19, wherein the calculating step further comprises applying a boundary limit to said mathematical function.

21. The method of claim 18, wherein the controlling step further comprises calculating the delivered stimulation frequency according to a mathematical function of the type:

$$Fc(t)=K-(Tau/t).$$

22. The method of claim 19, wherein the comparing step further comprises determining whether the change from Fstart to Ftarget corresponds to an increasing frequency or a decreasing frequency, and wherein the controlling step further comprises calculating the delivered stimulation frequency by implementing a mathematical function of the type:

$Fc(t)=(Fstart-Ftarget)*e^{-t/Tau\_inc}+Ftarget$, for controlling a determined increasing frequency, and $Fc(t)=(Fstart-Ftarget)*e^{-t/Tau\_dec}+Ftarget$ for controlling a determined decreasing frequency, where Tau_inc is a control parameter corresponding to an increasing frequency from Fstart to Ftarget; and Tau_dec is a control parameter corresponding to a decreasing frequency from Fstart to Ftarget.

23. The method of claim 22, wherein the controlling step further comprises implementing said mathematical function to calculate cardiac escape intervals corresponding to the delivered stimulation frequency, and calculating a next escape interval by applying to an existing escape interval a variation:

$$dTc(t)=Tc^3(t)*[Fc(t)-Ftarget]/Tau,$$

where Tc(t)=1/Fc(t); Tau=Tau_inc, for an increasing frequency, and Tau=Tau_dec, for a decreasing frequency.

24. The method of claim 23, further comprising applying the variation dTc(t) only to a variable number (MULT) of escape intervals.

25. The method of claim 24, wherein the step of applying the variation dTc(t) to a variable number (MULT) of escape intervals, further comprises calculating the variation as:

$$dTc(t)=Round(MULT*Tc^3(t)*[Fc(t)-Ftarget]/Tau,$$

and providing the factor MULT based on an algorithm for selecting which of said escape intervals is to be changed by said variation.

26. The method of claim 25, wherein providing the factor MULT based on said algorithm further comprises:

incrementing the factor MULT when said variation applied to the preceding escape interval is null, resetting the factor MULT to 1 as soon as the said variation is non null, and resetting the factor MULT to 1 if the calculated stimulation frequency equals Ftarget.

27. The method of claim 26 further comprising limiting the variation of the controlled delivered stimulation frequency from one cycle to the following cycle to a maximal value.

28. The method of claim 26 further comprising limiting the variation of the controlled delivered stimulation frequency from one cycle to the following cycle to a maximal value of approximately 6 $mn^{-1}$.

29. In an implantable rate-adaptive cardiac pacemaker having a delivered stimulation frequency and a sensor to detect a control parameter representative of the physical activity of a patient, apparatus for controlling the delivered stimulation frequency comprising:

means for calculating a stimulation frequency corresponding to said sensed control parameter;

means for comparing an existing delivered stimulation frequency (Fstart) and a calculated stimulation frequency (Ftarget); and means for controlling the delivered stimulation frequency to change between Fstart and Ftarget as a dependent non-linear mathematical function of time that approximates a physiological cardiac rhythm change over time.

30. The apparatus of claim 29 wherein the controlling means further comprises means for calculating the delivered stimulation frequency as a mathematical function of the type:

$$Fc(t)=A*(1-B*e^{-t/Tau})+C,$$

where Fc(t) is the delivered stimulation frequency to be delivered by the pacemaker as a function of the time, t is the parameter of time, and A, B, C, and Tau are predetermined constants.

31. The method of claim 30, wherein the calculating means further comprises a boundary limit to said mathematical function.

32. The method of claim 29, wherein the controlling means further comprises means for calculating the delivered stimulation frequency as a mathematical function of the type:

$$Fc(t)=K-(Tau/t).$$

33. The apparatus of claim 30, wherein the comparing means further comprises means for determining whether the change from Fstart to Ftarget corresponds to an increasing frequency or a decreasing frequency, and wherein the controlling means further comprises means for calculating the delivered stimulation frequency as a mathematical function of the type:

$$Fc(t)=(Fstart-Ftarget)*e^{-t/Tau\_inc}+Ftarget,$$ for a determined increasing frequency, and $$Fc(t)=(Fstart-Ftarget)*e^{-t/Tau\_dec}+Ftarget$$ for a determined decreasing frequency, where Tau_inc is a control parameter corresponding to an increasing frequency from Fstart to Ftarget; and Tau_dec is a control parameter corresponding to a decreasing frequency from Fstart to Ftarget.

34. The method of claim 33, wherein the controlling means further comprises means for calculating successive cardiac escape intervals wherein a next escape interval is calculated by applying to an existing escape interval a variation:

$$dTc(t)=Tc^3(t)*[Fc(t)-Ftarget]/Tau,$$

where Tc(t)=1/Fc(t); Tau=Tau_inc, for an increasing frequency, and Tau=Tau_dec, for a decreasing frequency.

35. The apparatus of claim 34, wherein the escape interval calculating means operates to further add the variation dTc(t) only to a variable number (MULT) of escape intervals.

36. The apparatus of claim 35, wherein the escape interval calculating means operates to calculate the variation as:

$$dTc(t)=Round(MULT*Tc^3(t)*[Fc(t)-Ftarget]/Tau),$$

wherein the factor MULT has a value based on an algorithm for selecting which of said escape intervals is to be changed by said variation.

37. The method of claim 36, wherein said algorithm further comprises the operations of:

incrementing the factor MULT when said variation applied to the preceding escape interval is null, resetting the factor MULT to 1 as soon as the said variation is non null, and resetting the factor MULT to 1 if the calculated stimulation frequency equals Ftarget.

38. The apparatus of claim 37 further comprising means for limiting the variation of the controlled delivered stimulation frequency from one cycle to the following cycle to a maximal value.

39. The apparatus of claim 37 further comprising means for limiting the variation of the controlled delivered stimulation frequency from one cycle to the following cycle to a maximal value of approximately 6 $mn^{-1}$.

\* \* \* \* \*

UNITED STATES PATENT AND TRADEMARK OFFICE
CERTIFICATE OF CORRECTION

PATENT NO. : 5,645,574
DATED : July 8, 1997
INVENTOR(S) : Bouhour et al.

It is certified that error appears in the above-identified patent and that said Letters Patent is hereby corrected as shown below:

Column 9, line 64, after "frequency" insert --(Fstart)--.

Signed and Sealed this

Eighth Day of December, 1998

Attest:

BRUCE LEHMAN

Attesting Officer

Commissioner of Patents and Trademarks